United States Patent [19]

Anis

[11] Patent Number: 4,575,374
[45] Date of Patent: Mar. 11, 1986

[54] FLEXIBLE ANTERIOR CHAMBER LENS

[76] Inventor: Aziz Y. Anis, 7531 N. Hampton, Lincoln, Nebr. 68506

[21] Appl. No.: 467,034

[22] Filed: Feb. 16, 1983

[51] Int. Cl.⁴ .............................................. A61F 2/16
[52] U.S. Cl. ...................................................... 623/6
[58] Field of Search .............................................. 3/13

[56] References Cited

U.S. PATENT DOCUMENTS

| 4,159,546 | 7/1979 | Shearing | 3/13 |
| 4,316,293 | 2/1982 | Bayers | 3/13 |
| 4,363,143 | 12/1982 | Callahan | 3/13 |
| 4,418,431 | 12/1983 | Feaster | 3/13 |
| 4,437,194 | 3/1984 | Hahs | 3/13 |

OTHER PUBLICATIONS

Style 115 Shepard Universal A/C IOL, American IOL International (advertisement) (one page) 15542 Graham St., Huntington Beach, Calif., Dec. 29, 1981.
Lens Styles from Cilco (advertisement brochure) Cilco, Inc., 1616 13th Ave., Box 1680, Huntington, West Va. 25717, Oct. 1982, pp. 1 & 2 (Anterior Chamber Lenses on p. 2).

Primary Examiner—Ronald L. Frinks
Attorney, Agent, or Firm—Zarley, McKee, Thomte, Voorhees & Sease

[57] ABSTRACT

An anterior chamber lens implant is provided which is designed to be implanted in the eye after the natural lens of the eye has been surgically removed. In each of the three embodiments disclosed herein, the implants include a disc-shaped lens having four flexible holding members extending therefrom so as to be completely independently flexible of the other holding members. Each of the holding members of the lens implants includes leg portions and foot portions. The holding members are flexibly designed so as to be flexibly movable rearwardly, forwardly, inwardly and outwardly.

13 Claims, 9 Drawing Figures

FLEXIBLE ANTERIOR CHAMBER LENS

BACKGROUND OF THE INVENTION

This invention relates to an anterior chamber lens.

The human eye is a very complex organ comprising numerous interacting elements which gather, focus, and transmit light rays to nerve endings which eventually transmit the information to the brain for image perception. The eye includes a natural crystalline lens of avascular tissue, the transparency of which depends upon the critical regularity of its fibers and the balance of its chemical constituents. Obviously, there are enumerable factors which may interfere with lens makeup and thereby affect its transparent character. No matter what the reason, a condition of opacity in the lens, commonly called cataract, reduces the visual performance of the eye. When the visual performance is reduced to an unacceptable level, surgical cataract extraction becomes a necessity.

An eye without a lens, a condition called aphakia, is obviously defective from an optical point of view in as much as it cannot properly refract incident light rays. Aphakic correction may be accomplished in three ways:

(1) thick eye glasses worn in front of the eye;
(2) contact lenses worn on the eye; or
(3) artificial intraocular lens implant within the eye.

It is this latter procedure with which the instant invention is concerned.

The structure and procedure of installing an intraocular lens is very critical because the elements which make up the eye are extremely sensitive and subject to irreparable damage. Numerous experimental lens designs have been abandoned through the years because they caused corneal damage and other manifestations of intraocular irritation. For example, in the late 1940's and early 1950's, H. Ridley conducted clinical experiments with an artificial intraocular lens which included a lens portion having foot-like projections extending radially away therefrom. This device was placed in the posterior chamber with the feet extending between the ciliary processes and the base of the iris. The lens proved positionally unstable and resulted in unsatisfactory amounts of irritation.

Logically, the anterior chamber of the eye was next investigated as a possible location for the implant. Here again, efforts have been less than satisfactory because of irritation and positional instability.

The lens described in U.S. Pat. No. 3,673,616 comprises an anteriorly positioned lens with two supporting loops affixed thereto for arrangement behind the iris. A plurality of rods also project from the lens for arrangement in front of the iris. The iris expands and contracts between the rods and loops, but never completely expands beyond the space therebetween, thus holding the lens in position. The problems associated with a free-floating lens of this type are numerous. For example, the lens is not fixed in position and is therefore subject to a wide range of positional variation. Also, the iris is subjected in numerous locations to pressure necrosis caused by the rods rubbing against the iris.

Another device similar to that described immediately above is shown in U.S. Pat. No. 3,906,551. This particular prosthetic lens includes a pair of closely spaced apertures through which suturing threads are inserted for transversely fixing the lens in position.

U.S. Pat. No. 3,866,249 discloses a posteriorly positioned prosthetic lens which has a multiplicity of forwardly projecting prongs. During surgical implantation, the prongs are extended through the iris to anchor the lens in position. While this arrangement certainly maintains positional integrity, it, too, has distinct disadvantages. The great number of prongs extending through and over the iris promote undesirable irritational characteristics, and the numerous fixation points also have a tendency to distort the iris by pulling on it in numerous directions.

Finally, attention is directed to the lenses disclosed in U.S. Pat. Nos. 3,925,825; 3,913,148; and 3,922,728. Each of these patents teach a prosthetic lens structure which is, in one way or another, less than desirable in construction and use.

In an effort to remedy the problems associated with the prior art lens implants, applicant previously has been granted U.S. Pat. Nos. 4,143,427; 4,166,293 and 4,251,887. Other recent developments relating to implant lens may be found in U.S. Pat. Nos. 4,316,293 and 4,340,979.

Although the prior art devices have been used with some success, it has been found that the closed loops such as described in U.S. Pat. No. 4,316,293 do not provide the necessary stability due to the fact that pressure on one portion of the loop causes deflection of the entire loop. The same is also true for the "J" type loops such as illustrated in U.S. Pat. No. 4,340,979.

Therefore, it is a principal object of this invention to provide an improved anterior chamber lens.

A further object of the invention is to provide an anterior chamber lens wherein four holding or positioning members extend from the lens in such a manner so that each of the holding members provide independent suspension and support for the lens.

Still another object of the invention is to provide an anterior chamber lens wherein the four holding members may flex rearwardly, forwardly, upwardly and downwardly independently of each other.

Still another object of the invention is to provide an anterior chamber lens which will not cause irritation.

Still another object of the invention is to provide an anterior chamber lens which will remain in place even if pressure or force is inadvertently applied to one portion of the lens.

These and other objects will be apparent to those skilled in the art.

SUMMARY OF THE INVENTION

An anterior chamber lens implant is described which may be implanted in the eye after the natural lens of the eye has been removed. Although there are three embodiments of the invention described herein, all of the embodiments include a disc-shaped lens having a front face, a rear face, an outer peripheral edge including upper and lower ends, and first and second sides. Four flexible holding members extend from the lens in such a manner so as to be completely independently flexible of the other holding members. In one form of the invention, a pair of the holding members are secured to the upper peripheral edge of the lens with a pair of the holding members being secured to the lower peripheral edge of the lens. The upper holding members include leg portions which extend upwardly and inwardly from the lens and foot portions extending laterally outwardly therefrom. Likewise, the lower holding members each include leg portions which extend downwardly and inwardly from the lens and foot portions at the lower ends thereof which extend laterally outwardly therefrom. In the other two embodiments of the invention, the leg portions of the holding members are arcuate and are equally spaced along their length from the peripheral edge of the lens.

DESCRIPTION OF THE PREFERRED EMBODIMENT

Figure 3:
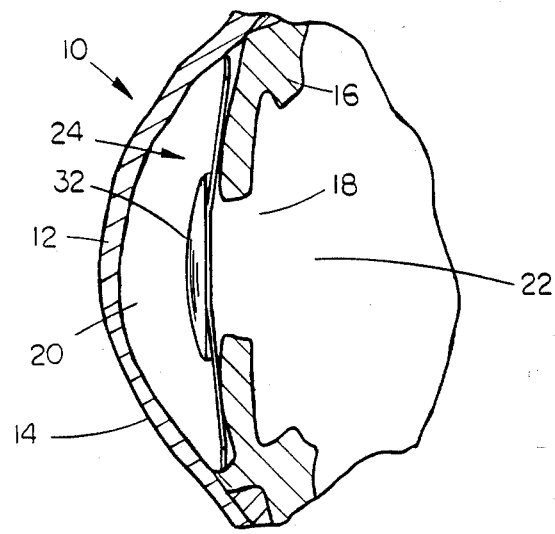
FIG. 3 is a sectional view of an eye showing the lens of this invention after implantation thereof.
Figure 6:
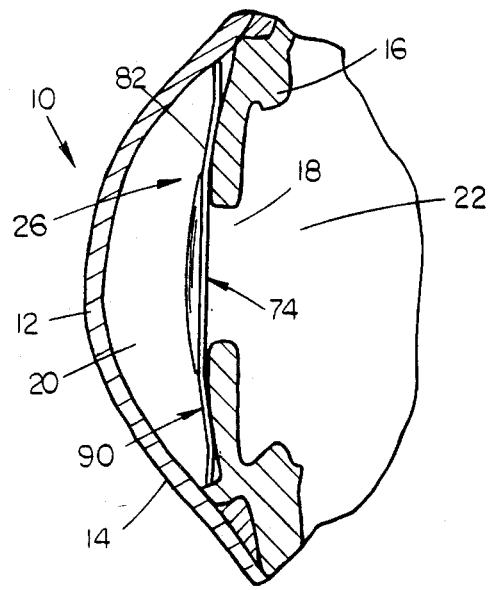
FIG. 6 is a sectional view of an eye showing the lens of FIGS. 4 and 5 after implantation thereof.
Figure 9:
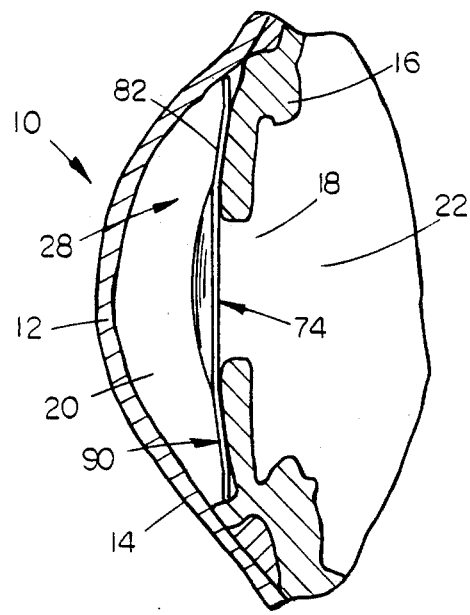
FIG. 9 is a sectional view of an eye showing the lens of FIGS. 7 and 8 after implantation thereof.

In FIGS. 3, 6 and 9, the numeral 10 refers to an eye, after cataract removal by surgical procedure. Eye 10 includes a cornea 12 which merges into an opaque protective covering 14 called sclera. Behind the cornea 12 is the iris 16 which defines a central opening 18 known as the pupil. The iris 16 comprises a muscular diaphragm-like element capable of expansion and contraction to control the amount of light passed therethrough. The iris divides the internal chamber of the eye into two chambers, the anterior chamber 20 and the posterior chamber 22. The natural crystalline lens of the eye would be located in the posterior chamber 22 adjacent to pupil 18.

Figure 1:
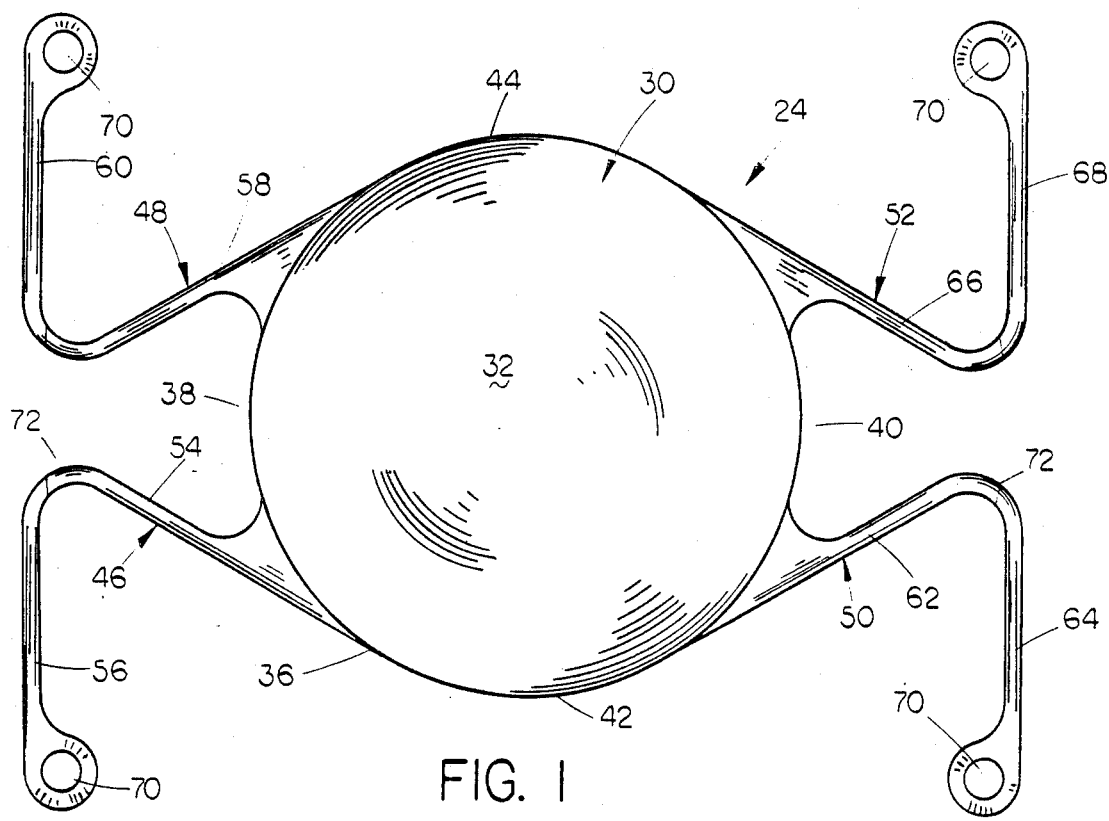
FIG. 1 is a plan view of one form of the lens.
Figure 2:
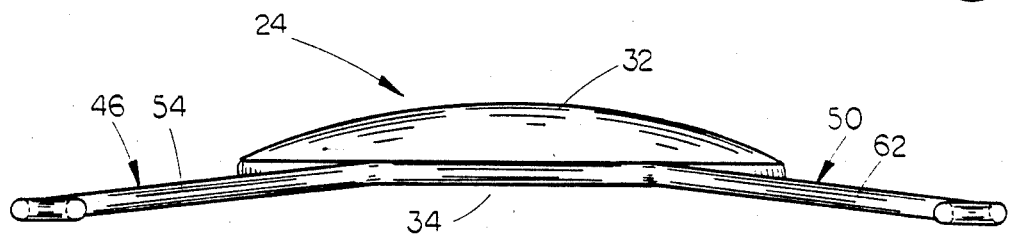
FIG. 2 is a side view of the lens of FIG. 1.
Figure 4:
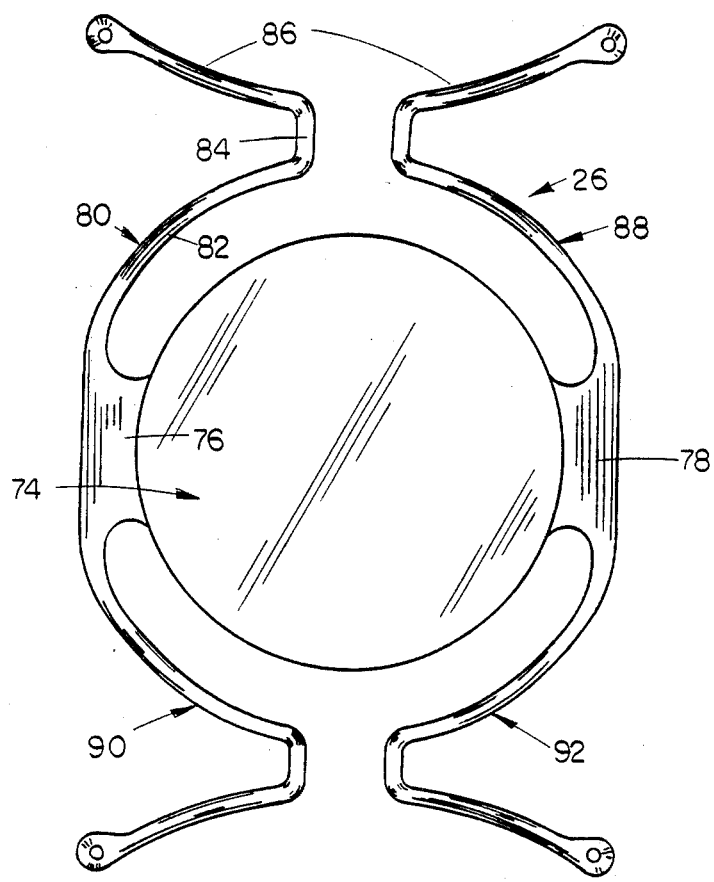
FIG. 4 is a plan view of a modified form of the lens.
Figure 5:
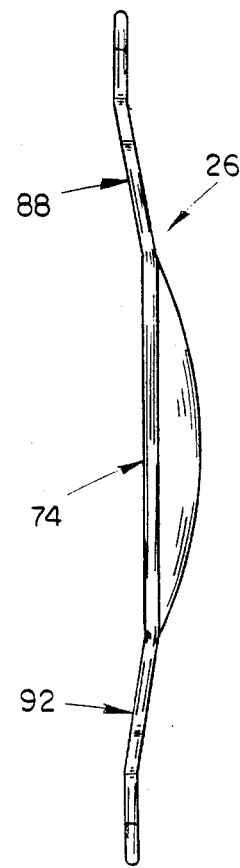
FIG. 5 is a side view of the lens of FIG. 4.
Figure 7:
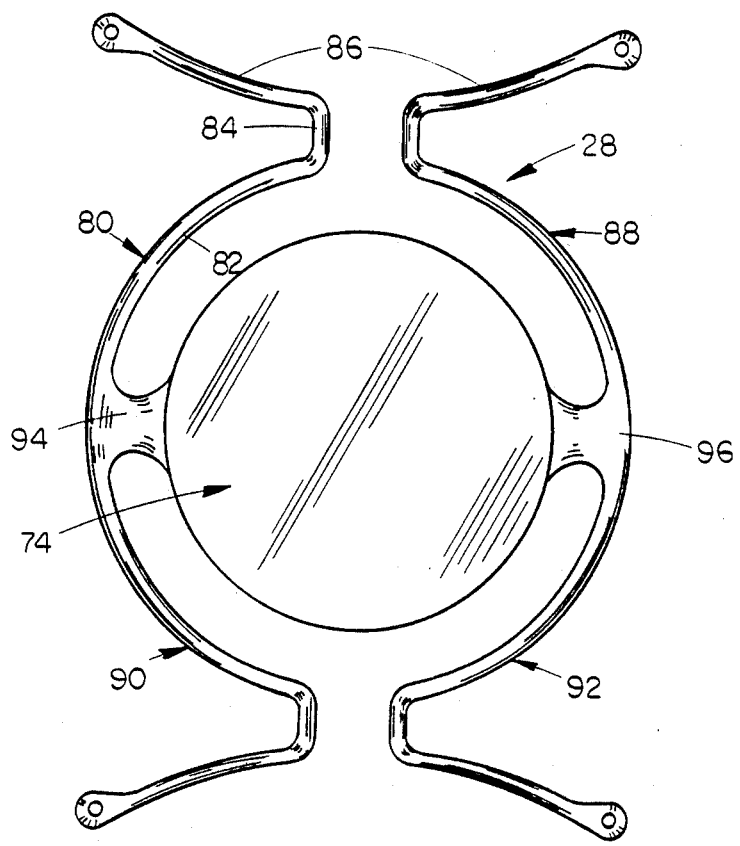
FIG. 7 is a plan view of still another modified form of the lens of this invention.
Figure 8:
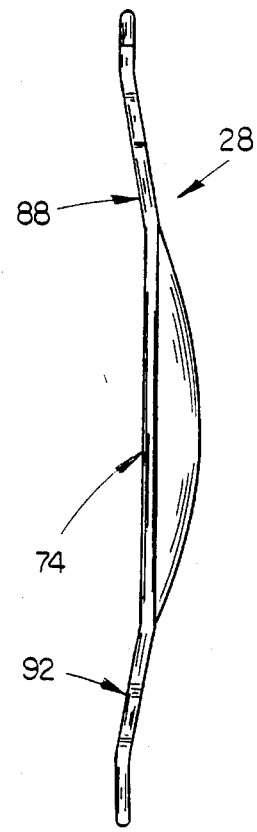
FIG. 8 is a side view of the lens of FIG. 7.

The lens implant 24 of FIGS. 1 and 2, the lens implant 26 of FIGS. 4 and 5, and the lens implant 28 of FIGS. 7 and 8 are each designed to be positioned within the anterior chamber 20 in contact with the forward portion of the iris 16 with the holding or fixation members impacting against the sclera spur in the angle of the anterior chamber.

Referring to FIGS. 1-3, lens implant 24 comprises a disc-shaped lens 30 having a front face 32, rear face 34, and an outer peripheral edge 36. For purposes of description, lens 32 will be described as having an upper end 38, lower end 40, and opposite sides 42 and 44.

Lens 30 is provided with four holding or fixation members 46, 48, 50 and 52 integrally formed therewith and which extend therefrom at approximately eleven o'clock, one o'clock, seven o'clock and five o'clock, respectively. Holding member 46 includes an elongated leg portion 54 extending inwardly and upwardly from peripheral edge 36 and a foot portion 56 which extends laterally outwardly from the upper end of leg portion 54. Similarly, holding member 48 includes leg portion 58 and foot portion 60. Holding member 50 is comprised of leg portion 62 and foot portion 64 while holding member 52 is comprised of leg portion 66 and foot portion 68. As seen in FIG. 1, the leg portions 54, 56, 62 and 66 extend from lens 32 insubstantially a tangential relationship with respect to the outer peripheral edge of the lens 32. As also seen in the drawings, the outer ends of the foot portions are provided with openings formed therein referred to generally by the reference numeral 70. FIG. 2 illustrates the fact that the leg portions of the holding elements also extend rearwardly as they extend outwardly from lens 32. As seen in FIG. 1, the juncture of each of the leg portions and foot portions is curved at 72 to permit the foot portion to flex upwardly and downwardly as well as rearwardly and forwardly with respect to the associated leg portion. The connection of the leg portions with the lens also permits the leg portions to flex inwardly and outwardly as well as rearwardly and forwardly with respect to the lens 30.

Referring to FIGS. 4-6, lens implant 26 includes a disc-shaped lens 74 having mounting projections 76 and 78 extending laterally therefrom at the opposite sides thereof. Lens 74 is identical to lens 32 except for the manner in which the holding elements are affixed thereto. Holding member 80 extends from projection 76 and comprises an arcuate leg portion 82 which extends upwardly and inwardly from projection 76. Intermediate portion 84 of holding member 80 extends upwardly from the upper end of leg portion 82. It can be seen in FIG. 4 that foot portion 86 extends upwardly and outwardly from the upper end of intermediate portion 84. It can also be seen in FIG. 4 that leg portion 82 is spaced from the outer peripheral edge of the lens element 74 and is generally arranged in a concentric fashion with respect thereto. Similarly, holding member 88 extends upwardly from projection 78 while holding members 90 and 92 extend downwardly from projections 76 and 78, respectively. The connection of the foot portions with the intermediate portions permit the foot portions to flex upwardly, downwardly, rearwardly or forwardly. Likewise, the leg portions of the holding members may also flex inwardly, outwardly, rearwardly or forwardly due to their connection with the projections 76 or 78.

The lens implant 28 of FIGS. 7-9 is substantially identical to lens implant 26 except that the mounting projections 94 and 96 in lens implant 28 have a vertical height slightly less than that of the mounting projections 76 and 78 in lens implant 26. Another difference between the lens implants 26 and 28 is that the outer portions of the projections 94 and 96 are arcuate or curved and dwell in substantially the same plane as the outside surfaces of the leg portions of the holding members.

Referring to the lens implant 24 of FIGS. 1-3, the lens 12 may be of any suitable diameter, but generally falls somewhere in the range of 6 millimeters. It should be realized that the parameters and ranges given herein are merely exemplary and that actual optical and surgical variables are subjectively determined by the opthamologic surgeon in charge of the patient. The lens 30 may be of any suitable material which may be made to exhibit the proper optical characteristics, and which is biologically inert. The most suitable material known for such lens implants is substantially polymethylmethacrylate, a compound commonly used in contact lens manufacture. Other suitable materials include quartz, opthalmic glass and polymeric materials. The overall length/diameter of the implant 24 is preferably 13.0 millimeters. The preferred width of the leg portions and foot portions of the implant 24 is 0.17 millimeters while the preferred thickness of the foot portions and leg portions is preferably 0.24 millimeters. The overall width of the implant 24 is preferably 8.0 to 8.5 millimeters.

Referring to the lens implant 26 of FIGS. 4-6, the overall length/diameter of the same is preferably 13.0 to 13.5 millimeters with the lens 74 preferably having a diameter of 5.5 millimeters. The preferred distance between the outer edges of the projections 76 and 78 is 7.0 millimeters thereby providing a width to the projections 76 and 78 of 0.75 millimeters. The preferred distance between the intermediate portions on the implant is 1.0 millimeters. The foot portions and leg portions of the lens implant 26 preferably have the same widths and thicknesses as that of lens implant 24.

Referring to the lens implant 28 of FIGS. 7-9, the dimensions thereof are substantially the same as the embodiment of FIGS. 4-6 with a few exceptions. In lens implant 28, the lens 74 preferably has a diameter of 5.0 millimeters with the distance between the outer edges of the projections 94 and 96 being preferably 7.0 millimeters which results in the width of the projections 94 and 96 being 1.0 millimeters.

In each of the lens implant embodiments, the lens thereof may generally have any suitable cross-sectional configuration; however, it has been found that a flat rear surface more easily accommodates an expanding and contracting pupil, and that the front surface thereof may be modified to provide the desired optical characteristics.

The lens implants of this invention are positioned in the anterior chamber of the eye through acceptable surgical procedures. When the implants are in position such as illustrated in FIGS. 3, 6 and 9, the foot portions thereof impact against the sclera spur in the angle of the anterior chamber. When the lens implants have been implanted, the foot portions thereof will exert sufficient force on the sclera spur to aid in maintaining the implant in position. Each of the holding members independently supports and suspends the implant in position to achieve the desirable positional stability. In the event that inadvertent pressure is applied to one of the holding members of the implant, that particular holding member will flex or deflect without adversely affecting the positional stability of the remaining holding members. Inadvertent pressure imposed on the lens itself will not cause objectionable movement of the holding members due to their flexible attachment to the lenses.

Thus it can be seen that the lens implant of this invention accomplishes at least all of its stated objectives.

I claim:
1. An anterior chamber lens, comprising,
   a disc-shaped lens having a front face, a rear face, an outer peripheral edge including upper and lower ends, and first and second sides,
   first, second, third and fourth flexible holding members extending from said lens,
   said first flexible holding member comprising a leg portion having inner and outer ends, said leg portion secured to said lens and extending upwardly and inwardly from said first side of said outer peripheral edge adjacent the upper end thereof in a substantial tangential relationship with respect to said peripheral edge, and a foot portion extending laterally outwardly from said outer end of said leg portion,
   said second flexible holding member comprising a leg portion having inner and outer ends, said leg portion secured to said lens and extending upwardly and inwardly from said second side of said outer peripheral edge adjacent the upper end thereof in a substantially tangential relationship with respect to said peripheral edge, and a foot portion extending laterally outwardly from said outer end of said leg portion,
   said third flexible holding member comprising a leg portion having inner and outer ends, said leg portion secured to said lens and extending downwardly and inwardly from said first side of said outer peripheral edge adjacent the lower end thereof in a substantially tangential relationship with respect to said peripheral edge, and a foot portion extending laterally outwardly from said outer end of said leg portion,
   said fourth flexible holding member comprising a leg portion having inner and outer ends, said leg portion secured to said lens and extending downwardly and inwardly from said second side of said outer peripheral edge adjacent the lower end thereof in a substantially tangential relationship with respect to said peripheral edge, and a foot portion extending laterally outwardly from said outer end of said leg portion,
   the outer ends of said leg portions terminating outwardly of the center line of said lens so that said first and second holding members are positioned at said first side of said lens and so that third and fourth holding members are positioned at said second side of said lens.
2. The structure of claim 1 wherein said leg portions of said holding members also extend rearwardly from said lens.
3. The structure of claim 1 wherein the juncture of each of said foot and leg portions is curved to permit the said foot portion to flex upwardly and downwardly with respect to the said leg portion.
4. The structure of claim 1 wherein each of said leg portions is flexibly connected to said lens to permit the leg portion to flex inwardly and outwardly.
5. The structure of claim 1 wherein said leg portions of said holding members extend from said lens at approximately the one o'clock, five o'clock, seven o'clock and eleven o'clock positions.
6. An anterior lens, comprising
   a disc-shaped lens having a front face, a rear face and an outer peripheral edge including upper and lower ends, and first and second sides,
   first, second, third and fourth flexible holding members extending from said lens,
   said lens having a first centrally positioned mounting protrusion extending outwardly from said first side,
   said lens having a second centrally positioned mounting protrusion extending outwardly from said second side,
   said first holding member comprising an arcuate leg portion extending inwardly and upwardly from said first mounting protrusion, an intermediate portion extending upwardly from the upper end of said leg portion, and a foot portion extending laterally outwardly from the upper end of said intermediate portion,
   said second holding member comprising an arcuate leg portion extending inwardly and upwardly from said second mounting protrusion, an intermediate portion extending upwardly from the upper end of said leg portion, and a foot portion extending laterally outwardly from the upper end of said intermediate portion,
   said third holding member comprising an arcuate leg portion extending inwardly and downwardly from said first mounting protrusion, an intermediate portion extending downwardly from the lower end of said leg portion and a foot portion extending laterally outwardly from the lower end of said intermediate portion, said fourth holding member comprising an arcuate leg portion extending inwardly and downwardly from said second mounting protrusion, an intermediate portion extending downwardly from the lower end of said leg portion, and a foot portion extending laterally outwardly from the lower end of said intermediate portion.

7. The structure of claim 6 wherein said leg portions also extend rearwardly from their respective mounting protrusions.

8. The structure of claim 6 wherein said leg portions are spaced from said outer peripheral edge of said lens in a generally concentric relationship.

9. The structure of claim 6 wherein said first and second foot portions also extend upwardly from the respective intermediate portions, and said third and fourth foot portions also extend downwardly from the respective intermediate portions.

10. The structure of claim 6 wherein said foot portions are flexibly secured to the respective intermediate portions to permit the foot portions to flex upwardly, downwardly, rearwardly and forwardly with respect thereto.

11. The structure of claim 6 wherein said leg portions are secured to said mounting protrusions to permit said leg portions to flex inwardly, outwardly, rearwardly and forwardly with respect thereto.

12. The structure of claim 6 wherein the outer ends of said first and second mounting protrusions are curved and dwell in substantially the same plane as the outside surfaces of said leg portions extending therefrom.

13. An anterior chamber lens, comprising
a disc-shaped lens having a front face, a rear face, an outer peripheral edge including upper and lower ends, and first and second sides,
a first flexible holding member including a leg portion extending upwardly and inwardly from said first side of said peripheral edge,
a second flexible holding member including a leg portion extending upwardly and inwardly from said second side of said peripheral edge,
a third flexible holding member including a leg portion extending downwardly and inwardly from said first side of said peripheral edge,
a fourth flexible holding member including a leg portion extending downwardly and inwardly from said second side of said peripheral edge,
each of said holding members having a foot portion extending outwardly from the inner ends of said leg portions, each of said holding members being independently flexible with respect to said lens,
each of said foot portions being independently flexible with respect to its associated leg portion.

* * * * *